(12) United States Patent
Faltys et al.

(10) Patent No.: US 7,561,920 B2
(45) Date of Patent: Jul. 14, 2009

(54) ELECTRIC AND ACOUSTIC STIMULATION FITTING SYSTEMS AND METHODS

(75) Inventors: Michael A. Faltys, Northridge, CA (US); Philip A. Segel, Englewood, CO (US); Edward H. Overstreet, Valencia, CA (US); William Vanbrooks Harrison, Valencia, CA (US)

(73) Assignee: Advanced Bionics, LLC, Valencia, CA (US)

( * ) Notice: Subject to any disclaimer, the term of this patent is extended or adjusted under 35 U.S.C. 154(b) by 670 days.

(21) Appl. No.: 11/097,611

(22) Filed: Mar. 31, 2005

(65) Prior Publication Data

US 2005/0245991 A1    Nov. 3, 2005

Related U.S. Application Data

(60) Provisional application No. 60/559,297, filed on Apr. 2, 2004.

(51) Int. Cl.
 *A61N 1/18* (2006.01)
(52) U.S. Cl. ............................. 607/57; 607/55; 607/56
(58) Field of Classification Search ............... 607/55–57
 See application file for complete search history.

(56) References Cited

U.S. PATENT DOCUMENTS 3,751,605 A    8/1973  Michelson
4,051,330 A    9/1977  Cole
4,400,590 A    8/1983  Michelson
4,819,647 A    4/1989  Byers et al.
5,033,090 A    7/1991  Weinrich
5,201,006 A    4/1993  Weinrich
5,204,917 A    4/1993  Arndt et al.
5,357,576 A    10/1994 Arndt
5,601,617 A    2/1997  Loeb et al.
5,626,629 A    5/1997  Faltys et al.
5,776,179 A    7/1998  Ren et al.
5,938,691 A    8/1999  Schulman et al.
6,067,474 A    5/2000  Schulman et al.
6,129,753 A    10/2000 Kuzma
6,157,861 A    12/2000 Faltys et al.
6,219,580 B1   4/2001  Faltys et al.
6,249,704 B1   6/2001  Maltan et al.
6,289,247 B1   9/2001  Faltys et al.
6,415,185 B1   7/2002  Maltan
6,522,764 B1   2/2003  Bøgeskov-Jensen
6,658,125 B1   12/2003 Batting
6,700,983 B1   3/2004  Bøgeskov-Jensen et al.

OTHER PUBLICATIONS

Related U.S. Appl. No. 10/218,645, filed Aug. 13, 2002.
Related U.S. Appl. No. 10/647,372, filed Aug. 25, 2003.
Related U.S. Appl. No. 10/651,653, filed Aug. 29, 2003.

*Primary Examiner*—Carl H Layno
*Assistant Examiner*—Deborah Malamud
(74) *Attorney, Agent, or Firm*—Henricks, Slavin & Holmes LLP

(57) ABSTRACT

Methods and systems for modifying the parameters of at least one hearing device for a patient with residual hearing provide needed orchestration of acoustic and electric stimulation of patients wearing such devices.

10 Claims, 9 Drawing Sheets

ELECTRIC AND ACOUSTIC STIMULATION FITTING SYSTEMS AND METHODS

CROSS-REFERENCE TO RELATED APPLICATIONS

This application claims the benefit of U.S. Provisional Application No. 60/559,297, filed on Apr. 2, 2004, which application is incorporated herein by reference.

FIELD OF THE INVENTION

The present invention relates to cochlear implant systems and methods, and more particularly relates to methods and systems for modifying the parameters of at least one hearing device for a patient with residual hearing.

BACKGROUND OF THE INVENTION

The present invention is related to U.S. patent application Ser. No. 10/218,645, filed Aug. 13, 2002, Ser. No. 10/647,372, filed Aug. 25, 2003, and Ser. No. 10/651,653, filed Aug. 29, 2003; all of which share the sole common assignee, Advanced Bionics Corporation of Valencia, Calif., and are hereby incorporated by reference in their respective entireties into the description of the present invention.

Cochlear prostheses, or cochlear implants, produce sensations of sound in deaf or partially-deaf patients by direct electrical stimulation of the auditory nerve. Cochlear implants have been used in conjunction with hearing aids for partially deaf patients. In modern, multichannel cochlear implants, several different sites are stimulated at various distances along the cochlea to evoke the different pitches of sound perception that are normally encoded by nerve activity originating from the respective sites. The patterns of electrical stimulation are derived from acoustic signals picked up by a microphone and transformed by a so-called speech processor that is programmed to meet the particular requirements of each patient. Several different schemes, or fitting techniques and/or systems as described below, for processing the acoustic signal and transforming it into electrical stimuli have been developed and are well-described in the scientific literature and various patents.

Electrical stimulation of predetermined locations within the cochlea of the human ear through an intra-cochlear electrode array is described, e.g., in U.S. Pat. No. 4,400,590. The electrode array shown in the '590 patent comprises a plurality of exposed electrode pairs spaced along and imbedded in a resilient curved base for implantation in accordance with a method of surgical implantation, e.g., as described in U.S. Pat. No. 3,751,605. The system described in the '590 patent receives audio signals, i.e., sound waves, at a signal processor (or speech processor) located outside the body of a hearing impaired patient. The speech processor converts the received audio signals into modulated RF data signals that are transmitted through the patient's skin and then by a cable connection to an implanted multi-channel intra-cochlear electrode array. The modulated RF signals are demodulated into analog signals and are applied to selected ones of the plurality of exposed electrode pairs in the intra-cochlear electrode so as to electrically stimulate predetermined locations of the auditory nerve within the cochlea.

U.S. Pat. No. 5,938,691, incorporated herein by reference, shows an improved multi-channel cochlear stimulation system employing an implanted cochlear stimulator (ICS) and an externally wearable speech processor (SP). The speech processor employs a headpiece that is placed adjacent to the ear of the patient, which receives audio signals and transmits the audio signals back to the speech processor. The speech processor receives and processes the audio signals and generates data indicative of the audio signals for transcutaneous transmission to the implantable cochlear stimulator. The implantable cochlear stimulator receives the transmission from the speech processor and applies stimulation signals to a plurality of cochlear stimulating channels, each having a pair of electrodes in an electrode array associated therewith. Each of the cochlear stimulating channels uses a capacitor to couple the electrodes of the electrode array.

A new, more sophisticated, class of cochlear implant, referred to as a bionic ear, is now available, providing patients with enhanced hearing performance. For example, Advanced Bionics Corporation, of Valencia, Calif., currently offers a cochlear implant which it refers to as the CII Bionic Ear® cochlear implant. Many features associated with the CII Bionic Ear implant are described in U.S. Pat. No. 6,219,580, incorporated herein by reference. The added complexity of the CII Bionic Ear cochlear implant includes higher numbers of channels, arbitrary simultaneous grouping, intra-phase gaps, binaural capabilities, and the like. The Bionic Ear implant contains advances in, e.g., internal memory banks, that enable it to send very detailed, high resolution sound signals to the auditory nerve. Such signals are delivered to the auditory nerve using a special electrode adapted to be inserted into the cochlea. A representative electrode usable with the CII Bionic Ear is described in U.S. Pat. No. 6,129,753, also incorporated herein by reference.

Other improved features of cochlear implant systems are taught, e.g., in U.S. Pat. Nos. 5,626,629; 6,067,474; 6,157,861; 6,249,704; and 6,289,247, each of which is incorporated herein by reference.

The implantable cochlear stimulators described in at least the '629, '474, '861, '580, and '704 patents are able to selectively control the pulse amplitude and pulse width of stimulating pulses that are applied through the electrode array to the cochlea, and the frequency at which the stimulating pulses are applied.

When a cochlear prosthesis is first provided to a patient, it is necessary to initially "fit" or "adjust" the prosthesis. As used herein, it should be noted that the terms "fit", "adjust", "fitting", "adjusting", "program", or "programming" relate to making electronic or software programming changes to the prosthesis, as opposed to making physical or hardware changes. Proper fitting allows the prosthesis to better perform its intended function of helping the patient to sense sound.

As the art of cochlear stimulation has advanced, the implanted portion of the cochlear stimulation system, and the externally wearable processor (or speech processor), have become increasingly complicated and sophisticated. In addition, much of the circuitry previously employed in the externally wearable processor has been moved to the implanted portion, thereby reducing the amount of information that must be transmitted from the external wearable processor to the implanted portion. The amount of control and discretion exercisable by an audiologist in selecting the modes and methods of operation of the cochlear stimulation system have increased dramatically and it is no longer possible to fully control and customize the operation of the cochlear stimulation system through the use of, for example, switches located on the speech processor. As a result, it has become necessary to utilize an implantable cochlear stimulator fitting system to establish the operating modes and methods of the cochlear stimulation system and then to download such programming into the speech processor. One such fitting system is described in the '629 patent. An improved fitting system is described in the '247 patent.

The '247 patent describes representative stimulation strategies (a.k.a., speech processing strategies) that may be employed by a multichannel stimulation system. Such strategies define patterns of stimulation waveforms that are to be applied to the electrodes as controlled electrical currents. For instance, the speech processing strategy is used, inter alia, to condition the magnitude and polarity of the stimulation current applied to the implanted electrodes of the electrode array. If multiple electrode pairs exist, as is the case with a multichannel cochlear stimulator, then the types of stimulation patterns applied to the multiple channels may be broadly classified as: (1) simultaneous stimulation patterns (substantially all electrodes receive current stimuli at the same time, thereby approximating an analog signal), or (2) sequential or non-simultaneous stimulation patterns (only one electrode receives a current pulse at one time). Simultaneous stimulation patterns may be "fully" simultaneous or partially simultaneous. A fully simultaneous stimulation pattern is one wherein stimulation currents, either analog or pulsatile, are applied to the electrodes of all of the available channels at the same time. A partially simultaneous stimulation pattern is one where stimulation currents, either analog or pulsatile, are applied to the electrodes of two or more channels, but not necessarily all of the channels, at the same time.

Acoustic transducers, such as earphone hearing instruments or hearing aids, can be used by patients with residual hearing in conjunction with cochlear prosthesis in either the same ear (ipsilater ear) as the cochlear implant or the opposite ear (contralateral ear). Examples of such acoustic transducers include U.S. Pat. Nos. 6,700,983; 6,658,125; 6,522,764; 5,201,006; 5,033,090; 5,357,576; 5,204,917; and 4,051,330; which patents are incorporated herein in their entireties by reference.

As mentioned above, auditory clinicians currently apply various systems and methods for modifying the various parameters of, or for fitting, cochlear prostheses. Similarly, auditory clinicians apply various systems and methods for modifying the various parameters of hearing aids. However, there are currently no established systems and methods which simultaneously or sequentially modify the parameters of both cochlear prostheses and hearing aids in a patient using both systems.

A need exists for a technique and system for programming, or fitting, a hearing device configured to deliver electric stimulation to a patient and a hearing device configured to deliver acoustic stimulation to the patient.

BRIEF SUMMARY OF THE INVENTION

The present invention is directed to fitting systems and techniques that may be used to fit a variety of cochlear implants and a variety of hearing aids, such as those mentioned above, during the same fitting session. The present invention addresses the above and other needs by providing a method for modifying the parameters of multiple hearing devices for a patient with residual hearing, a system for modifying the parameters of acoustic and electric stimulation hearing devices, and a method for modifying the parameters of at least one hearing device.

In an example embodiment, a method for modifying the parameters of at least one hearing device includes receiving electric and acoustic stimulation data from at least one hearing device to a computer with software, assessing electric and acoustic stimulation parameters and patterns based on the stimulation data, and delivering the electric and acoustic stimulation parameters and patterns to the at least one hearing device.

In another embodiment, the method further includes mapping the stimulation data with the software.

In another embodiment, assessing electric and acoustic stimulation parameters and patterns based on the stimulation data includes assessing the proper sequencing of acoustic and electric events for at least one of a hearing aid and the acoustic elements of an electric-acoustic processor and at least one of a cochlear implant speech processor and the electric elements of an electric-acoustic processor.

In another embodiment, delivering the electric and acoustic stimulation parameters and patterns to the at least one hearing device includes at least one of simultaneously and sequentially outputting instructions capable of modifying acoustic and electric parameters to determine interaction between multiple channels in at least one of a hearing aid, the acoustic elements of an electric-acoustic processor, a cochlear implant speech processor, and the electric elements of an electric-acoustic processor.

In another embodiment, the at least one hearing device comprises two hearing devices configured to be worn contralateral to each other by a patient.

In an example embodiment, a method for modifying the parameters of multiple hearing devices includes providing a user interface that allows a user to modify parameters of at least one of a hearing aid and the acoustic elements of an electric-acoustic processor and at least one of a cochlear implant speech processor and the electric elements of an electric-acoustic processor using software configured to provide instructions for at least one of acoustic stimulation to the hearing aid, electric stimulation to the cochlear implant speech processor, electric stimulation to the electric-acoustic processor, and acoustic stimulation to the electric-acoustic processor.

In another embodiment, the user interface is configured to allow the user to modify, with the software, the parameters of the electric-acoustic processor when the electric elements of the electric-acoustic processor are situated ipsilateral to the acoustic elements of the electric-acoustic processor.

In another embodiment, the software is configured to provide instructions when the at least one of the hearing aid and the acoustic elements of the electric-acoustic processor are situated contralateral to the at least one of the cochlear implant speech processor and the electric elements of the electric-acoustic processor.

In another embodiment, the method further includes mapping audio information to electrode contact position with the software in a patient with a cochlear implant.

In another embodiment, the method further includes at least one of simultaneously and sequentially outputting instructions capable of modifying acoustic and electric parameters to determine interaction between multiple channels in the at least one of the hearing aid, the acoustic elements of the electric-acoustic processor, the cochlear implant speech processor, and the electric elements of the electric-acoustic processor.

In another embodiment, the method further includes assessing, with the software, the proper sequencing of acoustic and electric events for at least one of the hearing aid and the acoustic elements of the electric-acoustic processor and at least one of the cochlear implant speech processor and the electric elements of the electric-acoustic processor.

In an example embodiment, a system for modifying the parameters of acoustic and electric stimulation hearing devices includes a computer provided with access to software that is configured to communicate with and modify parameters of at least one of a hearing aid and the acoustic elements of an electric-acoustic processor and at least one of a cochlear implant speech processor and the electric elements of an electric-acoustic processor.

In another embodiment, the system further includes a programming interface unit configured to exchange information between the computer and at least one of the hearing aid, the cochlear implant speech processor, the electric elements of the electric-acoustic processor, and the acoustic elements of the electric-acoustic processor.

In other embodiments, the computer is configured to communicate directly with at least one of the hearing aid, the cochlear implant speech processor, the electric elements of the electric-acoustic processor, and the acoustic elements of the electric-acoustic processor through wireless and/or wired communications.

In another embodiment, the computer is configured to display data used to at least one of map, evaluate, and modify the parameters of at least one of the hearing aid, the acoustic elements of the electric-acoustic processor, the cochlear implant speech processor, and the electric elements of the electric-acoustic processor.

In another embodiment, the software is scripted to evaluate data relevant to operational parameters of at least one of the hearing aid, the acoustic elements of the electric-acoustic processor, the cochlear implant speech processor, and the electric elements of the electric-acoustic processor.

In another embodiment, the software is configured to map parameter levels and ranges and is configured to map responses of a patient wearing the at least one of the hearing aid, the acoustic elements of the electric-acoustic processor, the cochlear implant speech processor, and the electric elements of the electric-acoustic processor.

In another embodiment, the computer is configured to simultaneously and sequentially output instructions capable of modifying acoustic and electric stimulation parameters to determine interaction between multiple channels in the at least one of the hearing aid, the acoustic elements of the electric-acoustic processor, the cochlear implant speech processor, and the electric elements of the electric-acoustic processor.

In another embodiment, the software is scripted to provide a suggested assessment of the proper sequencing of acoustic and electric events for at least one of the hearing aid and the acoustic elements of the electric-acoustic processor and at least one of the cochlear implant speech processor and the electric elements of the electric-acoustic processor.

BRIEF DESCRIPTION OF THE DRAWINGS

The above and other aspects of the present invention will be more apparent from the following more particular description thereof, presented in conjunction with the following drawings and appendices wherein.

Figure 1:
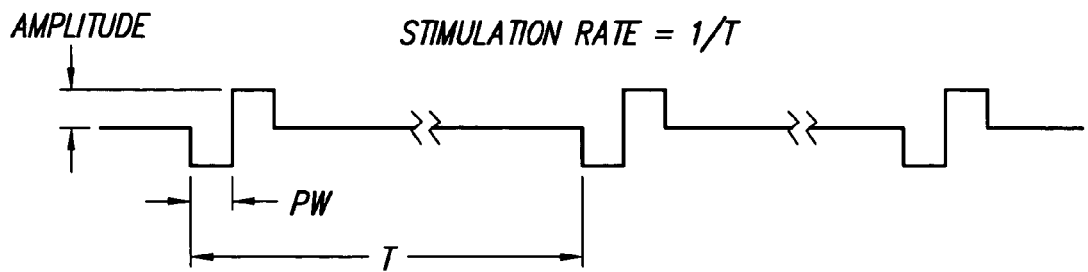
FIG. 1 is a current stimulation waveform that defines the stimulation rate (1/T) and biphasic pulse width (PW) associated with electrical stimuli, as those terms are used in the present application.

Appendix A, entitled "Manipulation of Sound Processor Parameters for Optimizing Bilateral—Hearing Aid/Cochlear Implant—Fittings: Interim Report", includes examples of methods and systems according to the present invention; and Appendix B, entitled "Manipulation of Sound Processor Parameters for Optimizing Bilateral—Hearing Aid/Cochlear Implant—Fittings", includes examples of methods and systems according to the present invention.

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

FIG. 1 shows a waveform diagram of a biphasic pulse train, and defines stimulation rate, pulse width and pulse amplitude.

Figure 2A:
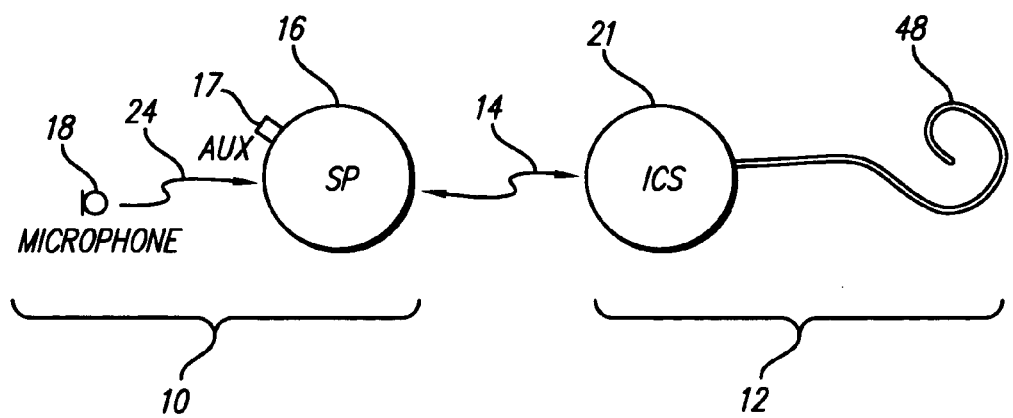
FIGS. 2A and 2B respectively show a cochlear implant system and a partial functional block diagram of the cochlear stimulation system, which system is capable of providing high rate pulsitile electrical stimuli.

FIG. 2A shows a cochlear stimulation system, or cochlear prosthesis, that includes a speech processor portion 10 and a cochlear stimulation portion 12. The speech processor portion 10 includes a speech processor (SP) 16 and a microphone 18. The microphone 18 may be connected directly to the SP 16, or may be coupled to the SP 16 through an appropriate communication link 24. An auxiliary input port 17 may also be part of the speech processor 16 to allow input signals from a source other than the microphone 18 to be input into the SP 16.

The cochlear stimulation portion 12 includes an implantable cochlear stimulator (ICS) 21 and an electrode array 48. The electrode array 48 is adapted to be inserted within the cochlea of a patient. The array 48 includes a multiplicity of electrodes, e.g., sixteen electrodes, spaced along its length that are selectively connected to the ICS 21. The electrode array 48 may be substantially as shown and described in U.S. Pat. Nos. 4,819,647 or 6,129,753, incorporated herein by reference. Electronic circuitry within the ICS 21 allows a specified stimulation current to be applied to selected pairs or groups of the individual electrodes included within the electrode array 48 in accordance with a specified stimulation pattern, defined by the SP 16.

The ICS 21 and the SP 16 are shown in FIG. 2A as being linked together electronically through a suitable data or communications link 14. In some cochlear implant systems, the SP 16, auxiliary input port 17 and microphone 18 comprise the external portion of the cochlear implant system; and the ICS 21 and electrode array 48 comprise the implantable portion of the system. In an example embodiment, the data link 14 is a transcutaneous data link that allows power and control signals to be sent from the SP 16 to the ICS 21. In some embodiments, data and status signals may also be sent from the ICS 21 to the SP 16.

In some cochlear implant systems, as shown more particularly below in FIG. 2B, at least certain portions of the SP 16 are included within the implantable portion of the overall cochlear implant system, while other portions of the SP 16 remain in the external portion of the system. In various embodiments, at least the microphone 18 (and auxiliary input port 17, if used) and associated analog front end (AFE) circuitry 22 are part of the external portion of the system, and at least the ICS 21 and electrode array 48 are part of the implantable portion of the invention. As used herein, "external" means not implanted under the skin or residing within the inner ear. However, "external" may mean within the outer ear, including in the ear canal, and may also include within the middle ear.

Typically, where a transcutaneous data link is to be established between the external portion and implantable portions of the system, such a link is realized by an internal antenna coil within the implantable portion and an external antenna coil within the external portion. In use, the external antenna coil is positioned so as to be aligned over the location where the internal antenna coil is implanted allowing the coils to be inductively coupled to each other, thereby allowing data (e.g., the magnitude and polarity of sensed acoustic signals) and power to be transmitted from the external portion to the implantable portion. Note, in other embodiments, both the SP 16 and the ICS 21 are implanted within the patient, either in the same housing or in separate housings. If in the same housing, the link 14 can be realized with a direct wire connection within such housing. If in separate housings, as taught, e.g., in U.S. Pat. No. 6,067,474, incorporated herein by reference, the link 14 can be, for example, an inductive link using a coil or a wire loop coupled to the respective parts.

The microphone 18 senses acoustic signals and converts such sensed signals to corresponding electrical signals, and thus can be considered an acoustic transducer. The electrical signals are sent to the SP 16 over a suitable electrical or other link 24. Alternatively, electrical signals can be input directly into the auxiliary input port 17 from a suitable signal source. The SP 16 processes the converted acoustic signals received from the microphone, or the electrical signals received through the auxiliary input port 17, in accordance with a speech processing strategy (e.g., a selected speech processing strategy) in order to generate appropriate control signals for controlling the ICS 21. In operation, by way of example, such control signals specify or define the polarity, magnitude, location (which electrode pair receives the stimulation current), and timing (when the stimulation current is applied to the electrode pair) of the stimulation current that is generated by the ICS. Such control signals thus combine to produce a desired spatiotemporal pattern of electrical stimuli in accordance with the desired speech processing strategy. Unlike early cochlear implant systems, cochlear implant systems according to various embodiments of the present invention advantageously confine such control signals to circuitry within the implantable portion of the system, thereby avoiding the need to continually send or transmit such control signals across a transcutaneous link.

The speech processing strategy is used, inter alia, to condition the magnitude and polarity of the stimulation current applied to the implanted electrodes of the electrode array 48. A typical speech processing strategy involves defining a pattern of stimulation waveforms that are to be applied to the electrodes as controlled electrical currents. In accordance with an example embodiment of the present invention, an auto-conditioning with high resolution (ACHR) strategy is used which stimulates the implanted electrodes with a high rate pulsitile pattern that is amplitude modulated by the sound information. If multiple electrode pairs exist, as is the case with a multichannel cochlear implant system, then the types of stimulation patterns applied to the multiple channels may be conveniently categorized as: (1) simultaneous stimulation patterns, or (2) non-simultaneous stimulation patterns. Simultaneous stimulation patterns may be "fully" simultaneous or partially simultaneous. A fully simultaneous stimulation pattern is one wherein stimulation currents, either analog or pulsitile, are applied to the electrodes of all of the available channels at the same time. A partially simultaneous stimulation pattern is one wherein stimulation currents, either analog or pulsitile, are applied to the electrodes of two or more channels, but not necessarily all of the channels, at the same time. Examples of each type are given in U.S. Pat. No. 6,289,247, incorporated herein by reference.

Analog waveforms used in analog stimulation patterns are typically reconstructed by the generation of continuous short monophasic pulses (samples). The sampling rate is selected to be fast enough to allow for proper reconstruction of the temporal details of the signal. An example of such a sampled analog stimulation pattern is a simultaneous analog sampler (SAS) strategy.

Current pulses applied in pulsitile stimulation patterns are generally biphasic pulses, as shown in FIG. 1, but can also be multiphasic pulses, applied to the electrodes of each channel. The biphasic/multiphasic pulse has a magnitude (e.g., amplitude and/or duration) that varies as a function of the sensed acoustic signal. (A "biphasic" pulse is generally considered as two pulses: a first pulse of one polarity having a specified magnitude, followed immediately, or after a very short delay, by a second pulse of the opposite polarity having the same total charge, which charge is the product of stimulus current times duration of each pulse or phase.) For multichannel cochlear stimulators, a high rate biphasic stimulation pulse train can be applied to each of the pairs of electrodes of selected channels in accordance with a selected strategy, and the pulse amplitude of the pulse train can be modulated as a function of information contained within the sensed acoustic signal or the received auxiliary input signal.

Figure 2B:
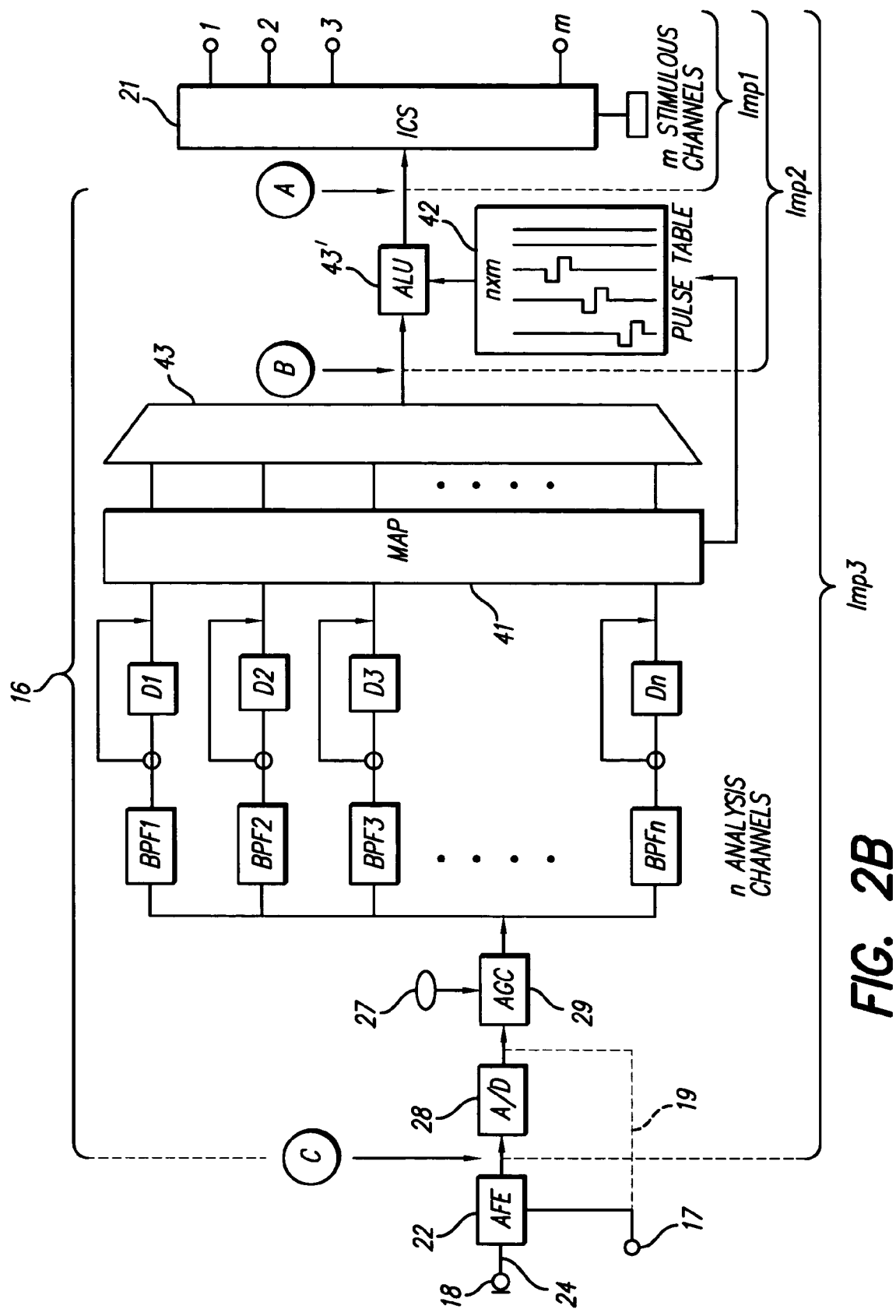

Turning next to FIG. 2B, a partial block diagram of a representative cochlear implant is shown. More particularly, FIG. 2B shows a partial functional block diagram of the SP 16 and the ICS 21 of an exemple cochlear implant system capable of providing a high rate pulsitile stimulation pattern. FIG. 2B depicts the functions that are carried out by the SP 16 and the ICS 21. The actual electronic circuitry used to carry out these functions is not critical to understanding and practicing the present invention. It should also be pointed out that the particular functions shown in FIG. 2B are representative of just one type of signal processing strategy that may be used (for dividing the incoming signal into frequency bands and independently processing each band). Other signal processing strategies can also be used to process the incoming acoustical signal.

A description of the functional block diagram of the cochlear implant system shown in FIG. 2B is provided in U.S. Pat. No. 6,219,580, incorporated herein by reference. It is to be appreciated that the functionality shown in FIG. 2B is only representative of one type of exemple cochlear implant system and is not intended to be limiting. The details associated with a given cochlear implant system are not critical to understanding and practicing the present invention.

In the manner described in the U.S. Pat. No. 6,219,580, the cochlear implant functionally shown in FIG. 2B provides n analysis channels that may be mapped to one or more stimulus channels. That is, as seen in FIG. 2B, after the incoming sound signal is received through the microphone 18 or auxiliary input port 17, and the analog front end circuitry (AFE) 22, it is digitized in an analog to digital (A/D) converter 28, and then subjected to appropriate gain control (which may include compression) in an automatic gain control (AGC) unit 29. (It should be noted that in some instances the signal input into the auxiliary input port 17 may already be digitized, in which case a signal path 19 is provided that bypasses the A/D converter 28.) After appropriate gain control, the signal is divided into n analysis channels, each of which includes a bandpass filter, BPFn, centered at a selected frequency. The signal present in each analysis channel is processed as described more fully in the U.S. Pat. No. 6,219,580, and the signals from each analysis channel are then mapped, using mapping function 41, so that an appropriate stimulus current, of a desired amplitude and timing, can be applied through a selected stimulus channel to stimulate the auditory nerve.

Thus it is seen that the system of FIG. 2B provides a multiplicity of channels, n, wherein the incoming signal is analyzed. The information contained in these n "analysis channels" is then appropriately processed, compressed and mapped in order to control the actual stimulus patterns that are applied to the patient by the ICS 21 and its associated electrode array 48. The electrode array 48 includes a multiplicity of electrode contacts, connected through appropriate conductors, to respective current generators, or pulse generators, within the ICS. Through this multiplicity of electrode contacts, a multiplicity of stimulus channels, e.g., m stimulus channels, exist through which individual electrical stimuli can be applied at m different stimulation sites within the patient's cochlea.

In various example embodiments, a one-to-one mapping scheme between the analysis channels and the stimulus channels is used, wherein n=m, and the signal analyzed in the first analysis channel is mapped to produce a stimulation current at the first stimulation channel, and so on. In other example embodiments, a different mapping scheme may prove beneficial to the patient. For example, assume that n is not equal to m (n, for example, could be at least 20 or as high as 32, while m may be no greater than sixteen, e.g., 8 to 16). The signal resulting from analysis in the first analysis channel can be mapped, using appropriate mapping circuitry 41 or the like, to the first stimulation channel via a first map link, resulting in a first stimulation site (or first area of neural excitation). Similarly, the signal resulting from analysis in the second analysis channel of the SP can be mapped to the second stimulation channel via a second map link, resulting in a second stimulation site. Also, the signal resulting from analysis in the second analysis channel can be jointly mapped to the first and second stimulation channels via a joint map link, which results in a stimulation site that is somewhere in between the first and second stimulation sites. The "in between site" can be referred to as a virtual stimulation site. Advantageously, this possibility of using different mapping schemes between n SP analysis channels and m ICS stimulation channels to thereby produce a large number of virtual and other stimulation sites provides a great deal of flexibility with respect to positioning the neural excitation areas in a location that proves most beneficial to the patient.

Still with reference to FIG. 2B, in various embodiments the speech processing circuitry 16 includes all of the circuitry from point (C) to point (A). In prior art cochlear implant systems, the entire SP circuitry was housed in a speech processor that was part of the external (or non-implanted) portion of the system. That is, in such prior art systems, only the ICS 21, and its associated electrode array, were implanted, as indicated by the bracket labeled "Imp1" (for "Implant-1"). This means that in such prior art systems, the signal passing through the serial data stream at point (A) is also the signal that must pass through the transcutaneous communication link from the external unit to the implanted unit. Because such a signal contains all of the defining control data for the selected speech processing strategy, for all m stimulation channels, it therefore has a fairly high data rate associated therewith. As a result of this high data rate, either the system operation must be slowed down, which is generally not desirable, or the bandwidth of the link must be increased, which is also not desirable because the operating power increases.

In contrast to prior art systems, a modern cochlear implant system, such as the CII Bionic Ear system, or the HiRes90K system, manufactured by Advanced Bionics Corporation of Sylmar, Calif., advantageously includes at least a portion of the speech processor 16 within the implanted portion of the system. For example, a cochlear implant system may place the Pulse Table 42 and arithmetic logic unit (ALU) 43 inside of the implanted portion, as indicated by the bracket labeled "Imp2" in FIG. 2B. Such partitioning of the speech processor 16 offers the advantage of reducing the rate of the data that must be passed from the external portion of the system to the implanted portion. That is, the data stream that must be passed to the implanted portion Imp2 comprises the signal stream at point (B). This signal is essentially the digitized equivalent of the modulation data associated with each of the n analysis channels, and (depending upon the number of analysis channels and the sampling rate associated with each) may be significantly lower than the data rate associated with the signal that passes through point (A). Hence, improved performance without sacrificing power consumption may be obtained with a bionic ear implant.

In other embodiments, cochlear implant systems may incorporate more and more of the speech processor 16 within the implanted portion of the system. For example, a fully implanted speech processor 16 would incorporate all of the SP in the implanted portion, as indicated by the bracket labeled Imp3 in FIG. 2B. Such a fully implanted speech processor offers the advantage that the data input into the system, i.e., the data stream that passes through point (C), need only have a data rate commensurate with the input signal received through the microphone 18 or the auxiliary input port 17.

Figure 3A:
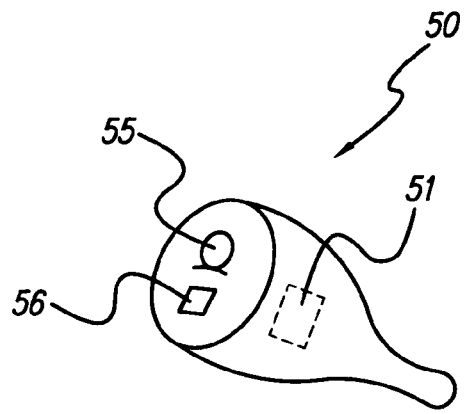
FIGS. 3A and 3B respectively show a conventional in-the-ear hearing aid and a behind-the-ear hearing aid.
Figure 3B:
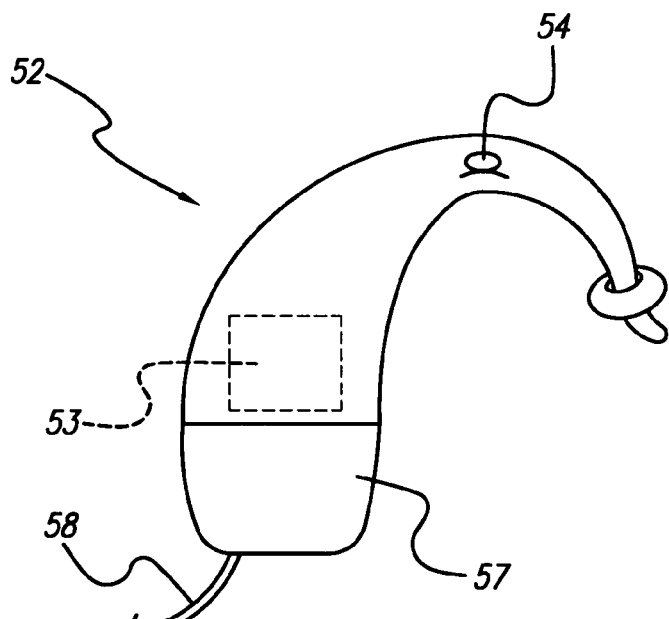

FIGS. 3A and 3B respectively show a conventional in-the-ear hearing aid 50 and a behind-the-ear hearing aid 52, such as those illustrated in U.S. Pat. Nos. 6,700,983; 6,658,125; 6,522,764; 5,201,006; 5,033,090; 5,357,576; 5,204,917; and 4,051,330; incorporated herein by reference. Both hearing aids 50 and 52 may include electronics 51 and 53 (e.g., such as those disclosed in the prior art) capable of controlling certain auditory stimulation parameters for a patient with residual hearing. Microphones 54 and 55 sense acoustic signals and convert the sensed signals to corresponding electrical signals, and thus may be considered acoustic transducers. The electrical signals are then output as amplified sound by the internal electronics 51 and 53 to the ear of a patient with residual hearing. Either hearing aid 50 or 52, or similar hearing aids, include optional input ports through which either auditory or electrical signals can be input to the hearing aids 50 or 52. In various embodiments, such input ports include a port 56 for a direct wire connection, a port for a wireless connection, a port in the form of an audio shoe 57 which attaches to either hearing aid 50 or 52 and includes a wire connection 58 or wireless connection to an auxiliary device. Auxiliary devices, such as the computer, palm pilot, and other interface units shown in FIGS. 4A-4C can thus communicate with the hearing aids 50 and 52 in order to read, map, evaluate, assess, and/or modify the operating acoustic stimulation parameters of the hearing aids 50 and 52. Thus, similar to the cochlear implant system described above, the parameters of a hearing aid system in various example embodiments are also programmed, or fit, to maximize the hearing experience of a patient.

Embodiments of the present invention can include an electric-acoustic processor in addition to, or as an alternative to, the cochlear implant systems and hearing aids described above. An electric-acoustic processor system, as with the example embodiment shown in FIG. 4C, can include any combination of the elements of cochlear implant systems and hearing aid systems, as needed, to facilitate a device capable of providing both acoustic stimulation signals to the acoustic sensing organs of the ear and electric stimulation signals to the auditory nerve of the same ear. Thus, in various embodiments, an electric-acoustic processor provides both acoustic and electric stimulation to the same ear of a patient with residual hearing. As with both the hearing aid system and the cochlear implant system described above, the electric-acoustic system can be programmed, or fit, to a particular patient so as to maximize or at least improve the hearing of that patient.

Embodiments of the present invention include systems and methods of reading, mapping, evaluating, assessing, and/or modifying, or fitting, the various electric and acoustic stimulation parameters of at least one hearing device (e.g., a hearing device similar to those described above). Many patients with residual, yet limited, hearing can employ a combination of devices that provide acoustic and electric stimulation. For example, a particular patient with residual hearing in one ear and profound deafness in another ear can use a hearing aid to amplify the sound in the ear with residual hearing and a cochlear implant system to provide electrical stimulation to the auditory nerve of the patient's profoundly deaf ear. Similarly, a patient can employ an electric-acoustic processor to provide both acoustic and electric stimulation to the auditory organs and auditory nerve of the same ear. These patients often suffer from a lack of coordination or orchestration of the various parameters of their various hearing devices.

For individuals with hearing sensitivity measure within normal limits, e.g., at frequencies of about <1 kHz, suboptimal hearing results may be produced by perceptual channel interaction between the various devices or by redundant acoustic information. Redundant acoustic information provided to the patient by the various devices may give rise to perceptual interference. Such interference makes it difficult for a patient to make sense of certain sounds and noises, thus decreasing the hearing comprehension of the patient. Thus, it is helpful to have techniques and systems that permit a clinician to orchestrate the acoustic and electric stimulation operations of a patient with residual hearing employing such devices so as to enhance the collective performance of these devices and maximize the hearing comprehension of the patient.

Figure 4A:
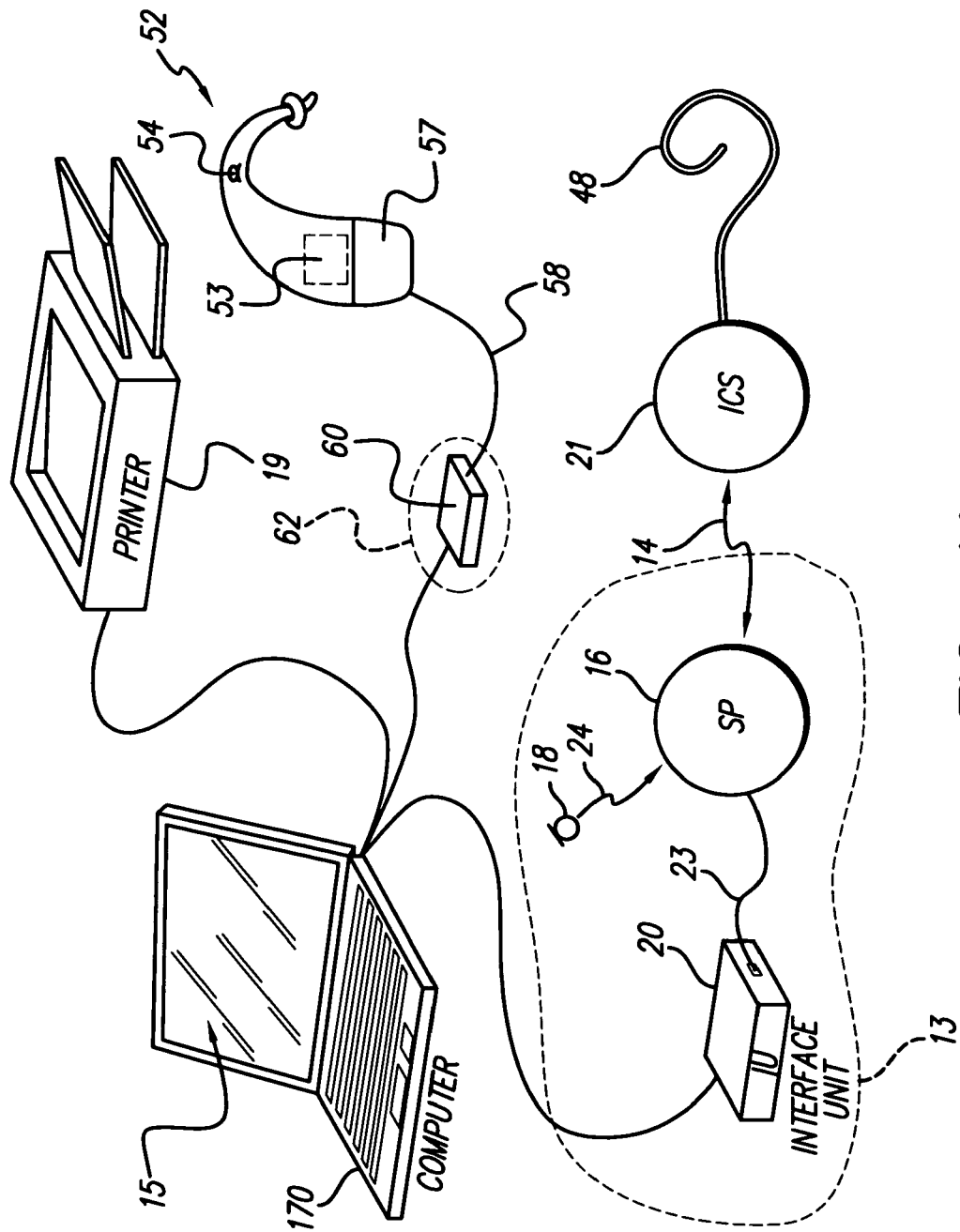
FIGS. 4A-4C show different example embodiments of fitting systems.
Figure 4B:
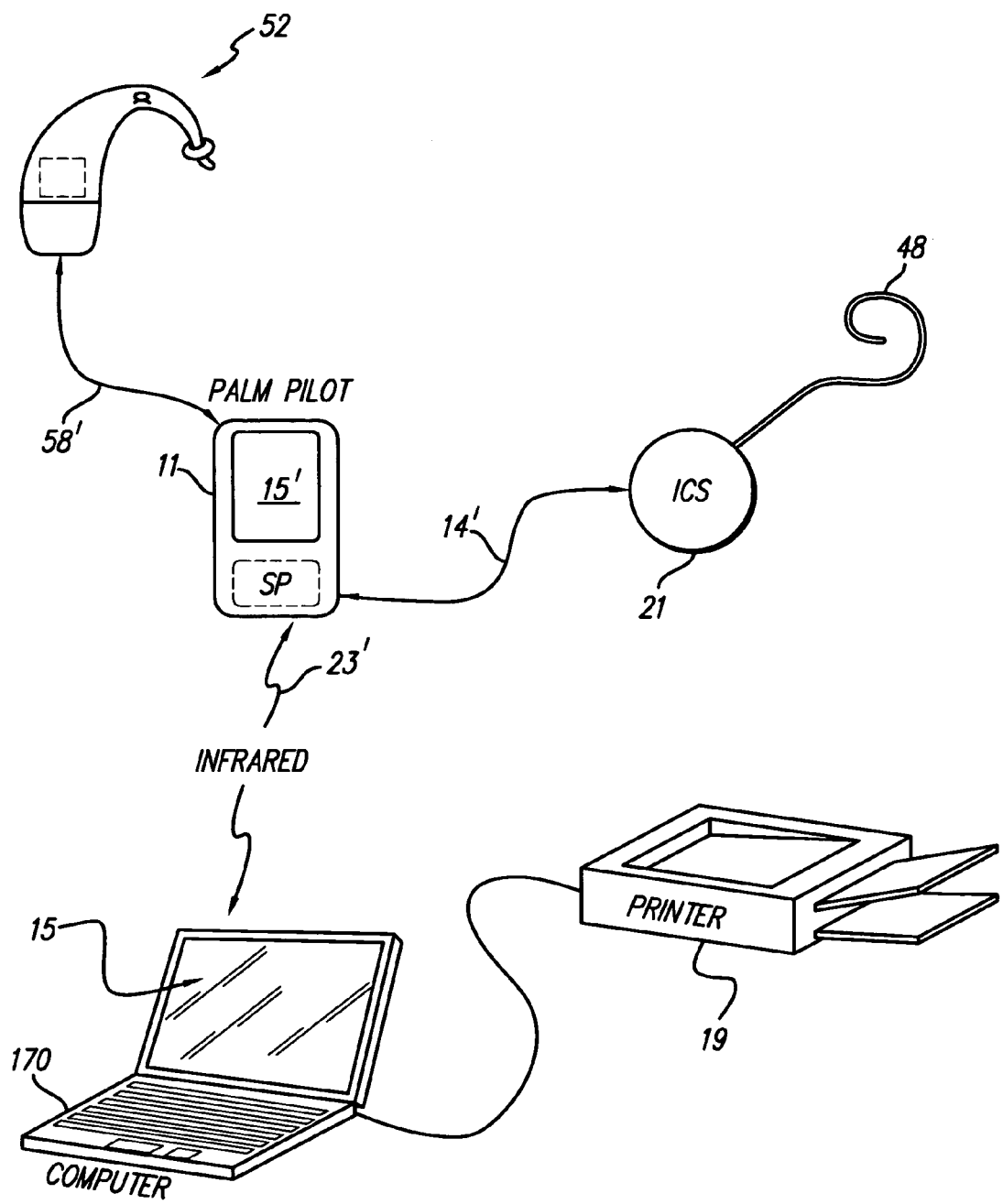
Figure 4C:
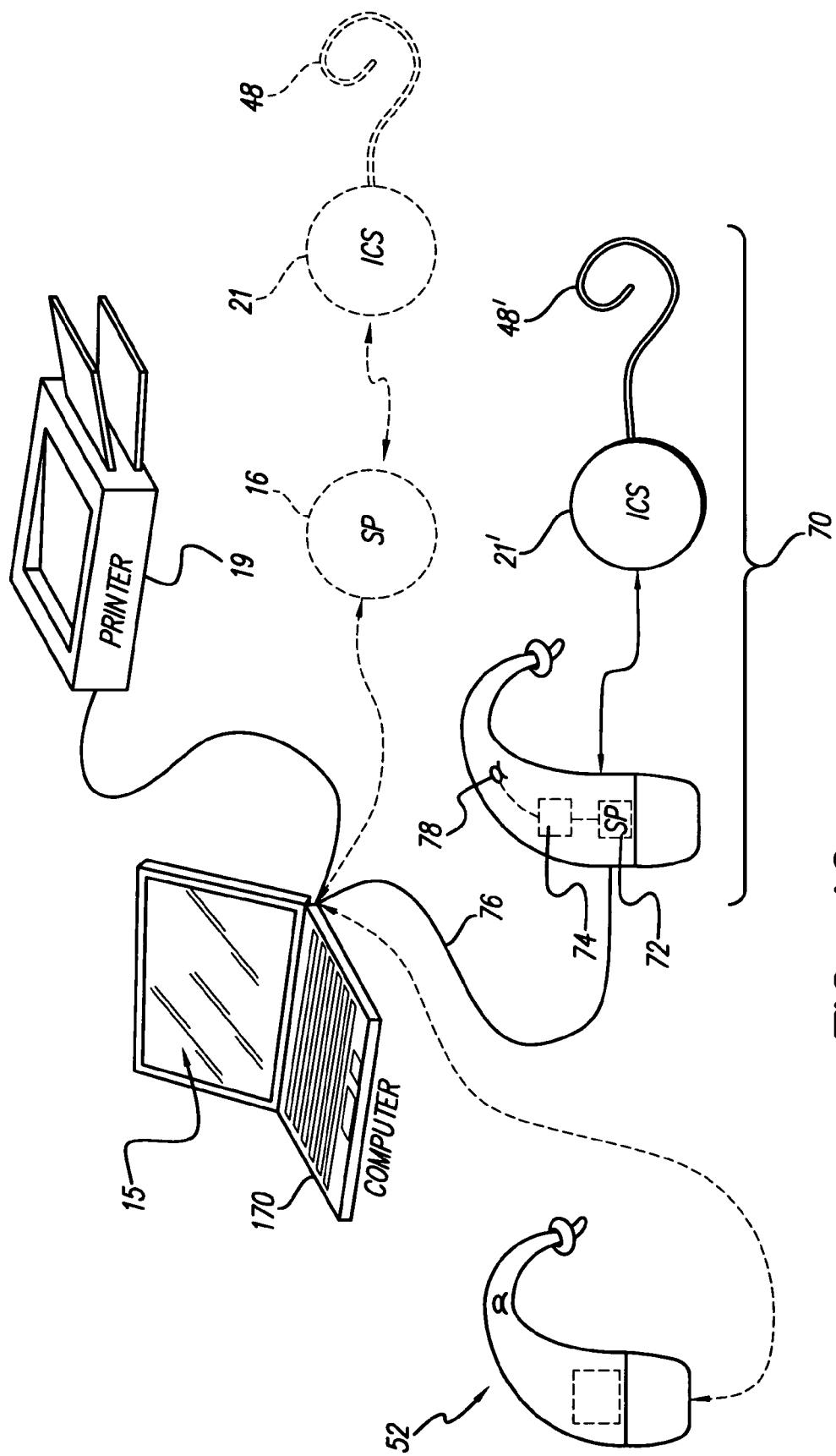

Example fitting system configurations are illustrated in FIGS. 4A-4C. These fitting configurations, or other configurations, can be used to provide orchestrated fitting or modification of acoustic and electric stimulation parameters of at least one hearing device, such as a cochlear implant, a hearing aid, or an electric-acoustic processor in a patient (e.g., with residual hearing).

FIG. 4A shows a diagram of basic components used to fit a patient with a cochlear implant system and a hearing aid. The cochlear implant system is as shown in FIG. 2A; and a SP 16 is linked to an ICS 21 which is connected to an electrode array 48. A microphone 18 is also linked to the SP 16 through a suitable communication link 24. A laptop computer 170, or other type of computer, or equivalent device, is coupled to the SP 16 through an interface unit (IU) 20, or equivalent device. The type of linkage 23 established between the IU 20 and the SP 16 can vary depending upon whether the SP 16 is implanted or not. Any suitable communications link 23 may be used, as is known in the art, and thus the details of the link 23 are not important for purposes of the present invention. It should be noted that in some embodiments, the IU 20 is included within the computer 170 (for example, as a communications interface already present within the computer, e.g., a serial port or other built-in port, or an IR port).

The computer 170, with or without the IU 20, provides input signals to the SP 16 that simulate acoustical signals sensed by the microphone 18 (or received through the auxiliary input port 17 (FIG. 2A) and/or provides command signals to the SP 16. In some instances, e.g., when testing the patient's threshold levels, the signals generated by the computer 170 replace the signals normally sensed through the microphone 18. In other instances, e.g., when testing the patient's ability to comprehend speech, the signals generated by the computer 170 provide command signals that supplement the signals sensed through the microphone 18.

Also as seen in FIG. 4A, the hearing aid system 52 is as shown in FIG. 3 and includes the internal electronics 53, the microphone 54, and the audio shoe, or boot, 57 with accompanying communications wire 58. The laptop computer 170, or other type of computer, or equivalent device, is coupled to the audio boot 57 through an audio interface unit (AIU) 60, or equivalent device. Any suitable communications link between the computer 170 and the AIU 60, and between the AIU 60 and the audio boot 57, can be used, as is known in the art, and thus the details of such interfaces are not important for purposes of the present invention. It should be noted that for some applications, the AIU 60 is included within the computer 170 (for example, as a communications interface already present within the computer, e.g., a serial port or other built-in port, or an IR port).

The computer 170, with or without the AIU 60 and/or audio boot 57, delivers signals to the electronics 53 of the hearing aid 52 that simulate acoustical signals sensed by the microphone 54. The computer 170 also delivers command signals to the electronics 53. In some instances, e.g., when testing the patient's threshold levels, the signals generated by the computer 170 replace the signals normally sensed through the microphone 54. In other instances, e.g., when testing the patient's ability to comprehend speech, the signals generated by the computer 170 provide command signals that supplement the signals sensed through the microphone 54.

In an example embodiment, the laptop computer 170 (or equivalent device) provides a display screen 15 on which selection screens, stimulation templates and other information may be displayed and defined. In such an embodiment, the computer 170 provides a mechanism for the audiologist or other medical personnel, or even the patient, to easily select and/or specify a particular pattern of stimulation parameters that can be used thereafter, even if for just a short testing period, regardless of whether the stimulation pattern is simple or complex. The various screens, templates, and other information can be separated for each respective hearing device being fitted for a patient. Alternatively, the screens, templates, and other information can be combined in a way that permits the individual controlling the fitting process to easily simultaneously or sequentially view and modify the parameters of the device(s) being fitted.

Also shown in FIG. 4A is a printer 19, or other auxiliary device, which may be connected to the computer 170, if desired, in order to allow needed support functions such as providing a record of the selection criteria, stimulation templates and pattern(s) that have been selected and/or specified to be printed.

FIG. 4B illustrates an alternative fitting system, in which the ICS 21 and the hearing aid 52 are linked to a speech processor configured or emulated within a palm personal computer (PPC) 11, such as a Palm Pilot, or equivalent processor, commercially available, e.g., from Hewlett Packard. In the illustrated example embodiment, the PPC 11 includes its own display screen 15' on which graphical and textual information can be displayed. In use, the PPC 11 is linked, e.g., through an infrared link 23', to another computer, 170, as necessary. By way of example, the functions of the SP and related devices (i.e., the functions that support fitting of the hearing aid 52) are stored in a flashcard (a removable memory card that can be loaded into the PPC 11), thereby enabling the PPC 11 to perform the same functions of those elements encircled by the dashed lines 13 and/or 62 in FIG. 4A. The PPC 11 is coupled to the ICS 21 through a suitable data/power communications link 14' and is coupled to the hearing aid 52 through a suitable data/power communications link 58'.

The ICS 21 and the hearing aid 52 of FIGS. 4A and 4B are suitable for being situated in the same ear (ipsilateral) or contralateral ears of a patient (e.g., with residual hearing).

FIG. 4C illustrates an alternative fitting system that can also be used with an electric-acoustic processor system 70 situated in one ear (ipsilateral) of a patient (e.g., with both residual hearing and the need for electrical stimulation for the same ear). In FIG. 4C, the electric-acoustic processor system 70 includes a speech processor 72 and internal acoustic electronics 74 which are linked with the computer 170 directly through wired or wireless data/power communications link 76. Alternatively, an auxiliary support unit (not shown) such as the IU 20 or AIU 60 of FIG. 4A can be used to supplement the communication link 76 between the system 70 and the computer 170. In this example embodiment, the system 70 also includes a microphone 78 capable of performing one or more of the microphone functions described in reference to the various embodiments of the present invention.

The computer 170 is configured with software to control reading, displaying, delivering, receiving, assessing, evaluating, and/or modifying both acoustic and electric stimulation data sent to the system 70. In an example embodiment, the electric-acoustic processor system 70 is configured to deliver both acoustic stimulation to the auditory sensory organs of the ear and electric stimulation to the auditory nerve of the same ear. Thus, the acoustic stimulation elements and the electrical stimulation elements interact with the computer 170 and other elements of systems of the present invention in a similar manner as the electric stimulation elements of a cochlear implant system and acoustic stimulation elements of a hearing aid as discussed through this description of the invention. In various embodiments, the acoustic and electric stimulation elements of the system 70 can alternatively act in a coordinated effort, e.g., under the direction of a program provided within the speech processor 72 or a similar memory element.

FIG. 4C further illustrates alternative embodiments wherein the speech processor 16 and the ICS 21 of a cochlear implant system and/or a hearing aid 52 can be simultaneously situated in a patient's ear contralateral to the electric-acoustic system 70. Other embodiments include a second electric-acoustic processor system situated in a patient's ear contralateral to the ear of the electric-acoustic system 70.

Figure 5:
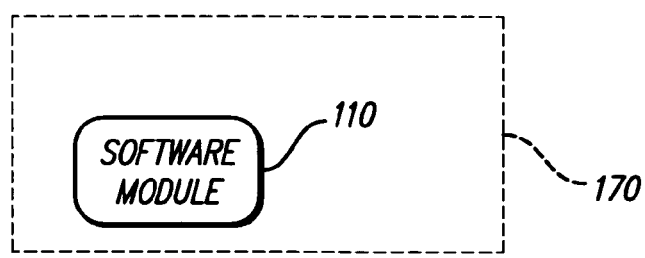
FIG. 5 shows a software module for generating stimuli used during the sound processor setting procedure (or fitting process)

As illustrated generally in FIG. 5, advantageously, all of the stimuli used during the sound processor setting procedure (or fitting process) can be generated through a software module 110 that is incorporated into the computer 170, or equivalent processor.

In another variation of the present invention, the software module, or equivalent processor, used to generate the stimuli used is acoustically linked with the microphones 18, 54, 55, and 78 used by the various hearing devices of the present invention (see FIGS. 4A-4C). That is, the modulated stimuli are, in some embodiments, inputted into the hearing devices via the microphone link rather than through an interface unit, an auxiliary port, or another direct connection between the computer 170 and the hearing devices.

In operation, the level of the stimuli provided during the fitting process can be adjusted according to known perceptual loudness contours derived from normal hearing individuals (minimal audible field) or from known acoustic phenomena, such as the long-term spectrum of speech. Thus, stimuli can be delivered at the electrical equivalent of the long-term spectrum of speech, at a level representing the detection abilities of normal hearing individuals, or at any point in between.

Examples of methods and systems according to the present invention are attached hereto and labeled as Appendix A, entitled "Manipulation of Sound Processor Parameters for Optimizing Bilateral—Hearing Aid/Cochlear Implant—Fittings: Interim Report", and Appendix B, entitled "Manipulation of Sound Processor Parameters for Optimizing Bilateral—Hearing Aid/Cochlear Implant—Fittings". Both of these documents (Appendices A and B) are incorporated herein by reference in their entireties.

Figure 6:
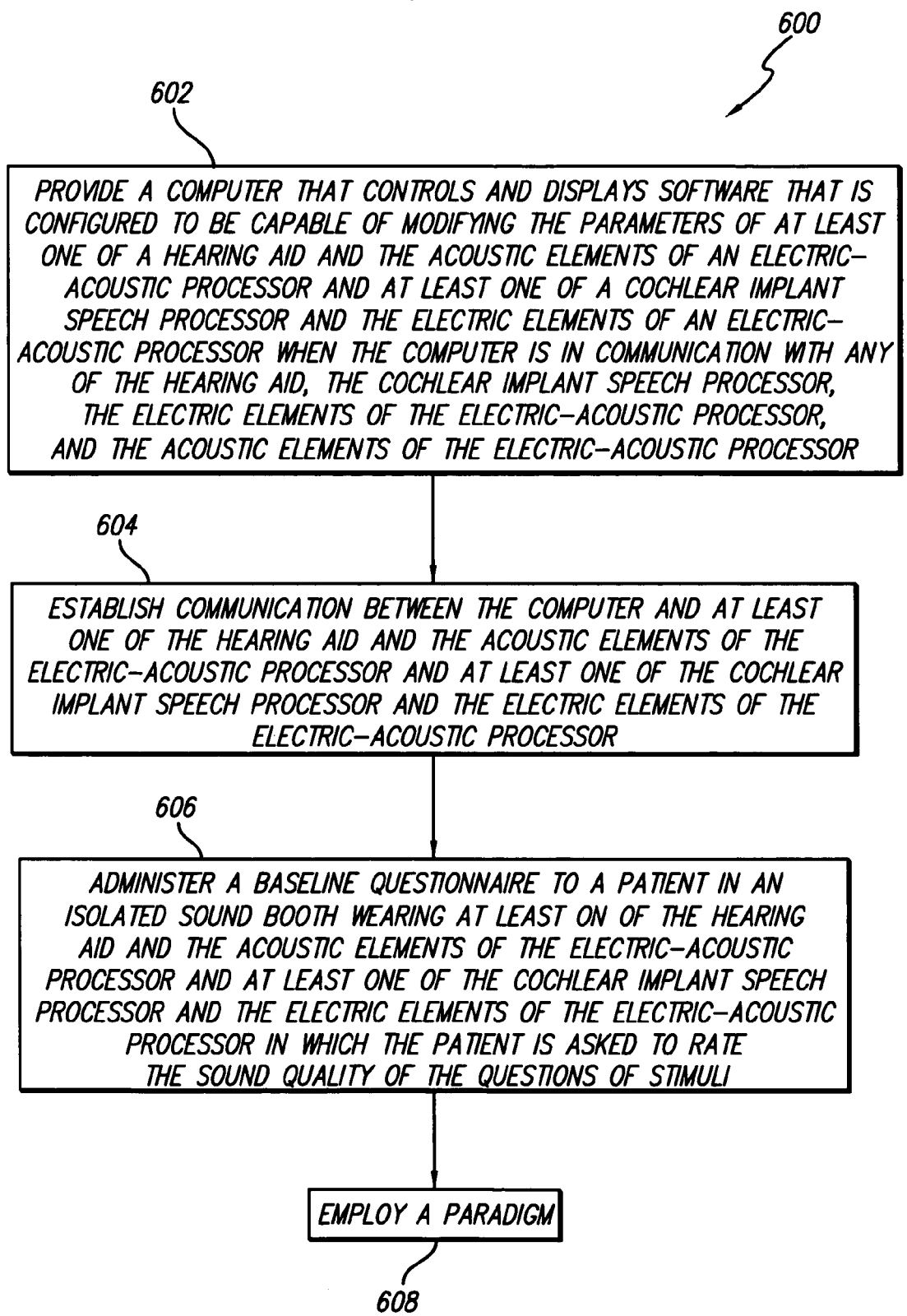
FIG. 6 is a flowchart of an example method for modifying the parameters of multiple hearing devices for a patient with residual hearing.

Referring to FIG. 6, in an example embodiment, a method 600 for modifying the parameters of multiple hearing devices for a patient with residual hearing includes the following steps which can be performed in any enabling order. At step 602, a computer is provided that controls and displays software that is configured to be capable of modifying the parameters of at least one of a hearing aid and the acoustic elements of an electric-acoustic processor and at least one of a cochlear implant speech processor and the electric elements of an electric-acoustic processor when the computer is in communication with any of the hearing aid, the cochlear implant speech processor, the electric elements of the electric-acoustic processor, and the acoustic elements of the electric-acoustic processor. At step 604, communication is established between the computer and at least one of the hearing aid and the acoustic elements of the electric-acoustic processor and at least one of the cochlear implant speech processor and the electric elements of the electric-acoustic processor. The software is used to provide instructions for at least one of acoustic stimulation to the hearing aid, electric stimulation to the cochlear implant speech processor, electric stimulation to the electric-acoustic processor, and acoustic stimulation to the electric-acoustic processor. At step 606, a baseline questionnaire is administered to a patient in an isolated sound booth wearing at least one of the hearing aid and the acoustic elements of the electric-acoustic processor and at least one of the cochlear implant speech processor and the electric elements of the electric-acoustic processor in which the patient is asked to rate the sound quality of the questions or stimuli, e.g., presented on a 5-point scale for each of the hearing devices respectively (the other hearing devices being turned off during the testing of a particular device) and then in combination in order to verify and set appropriate baseline settings. At step 608, at least one of the paradigms described in reference to FIGS. 7 and 8, or similar paradigms, are employed.

Figure 7:
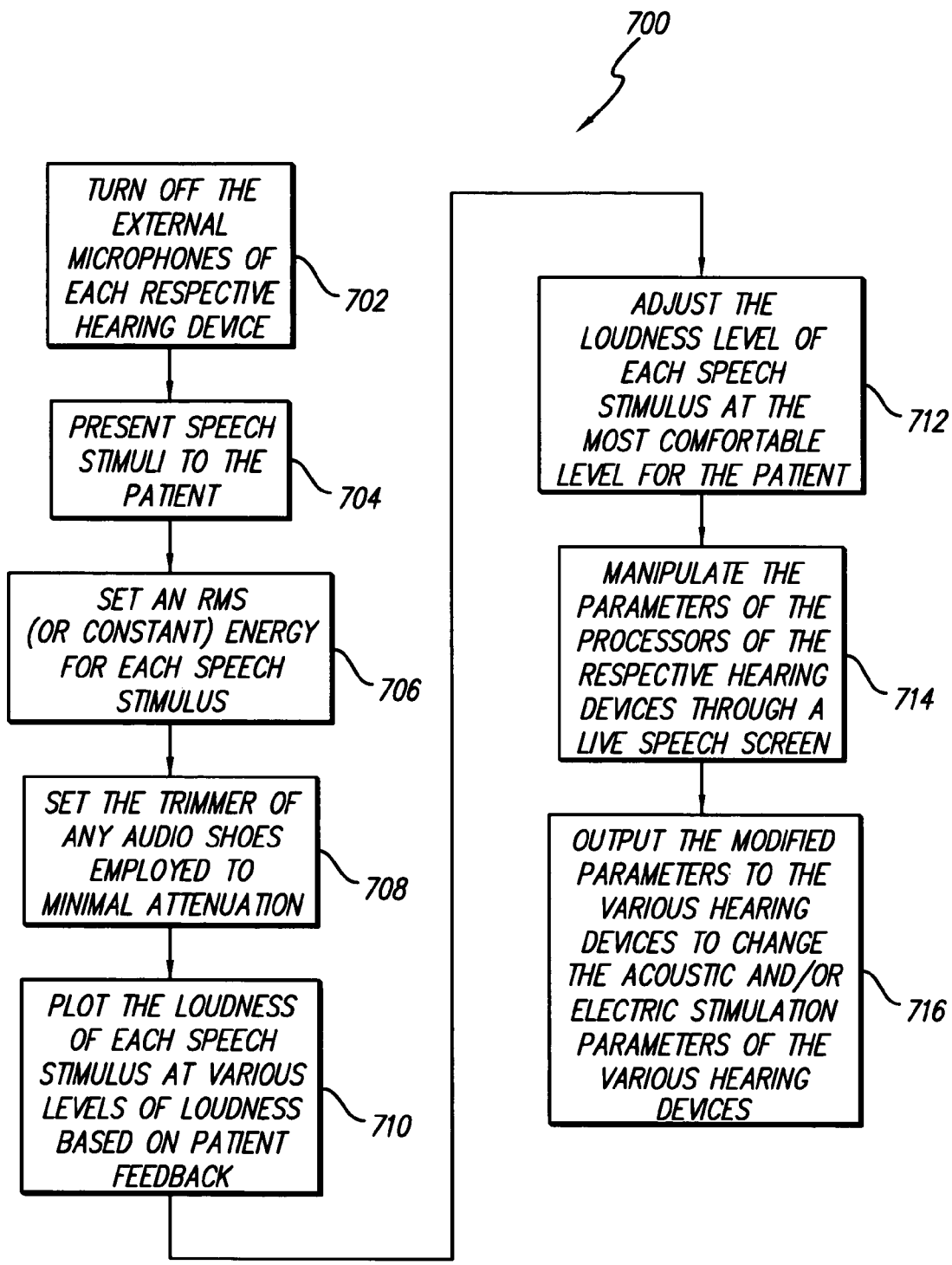
FIG. 7 is a flowchart of an example paradigm for the method of FIG. 6.

Referring to FIG. 7, in an example embodiment, a paradigm 700 includes the following steps which can be performed in any enabling order. At step 702, the external microphones of each respective hearing device are turned off so as to avoid unwanted environmental noise and sounds. At step 704, speech stimuli (such as the sounds of the Ling 5 sound test: /a/, /u/, /i/, /sh/, and /s/) from audio files on a computer are presented to the patient via direct connection from the computer to each of the hearing devices respectively and in combination. At step 706, an RMS (or constant) energy is set for each speech stimulus, for example, by routing the output of the computer through a manual attenuator (e.g., Pasternak 50B). At step 708, the trimmer of any audio shoes employed is set to minimal attenuation. At step 710, the loudness of each speech stimulus at various levels of loudness based on patient feedback is plotted. At step 712, the loudness level of each speech stimulus is adjusted at the most comfortable level for the patient. At step 714, the parameters of the processors of the respective hearing devices are manipulated through a live speech screen, e.g., shown in the output adjustment window of a software program presented on the computer. At step 716, the modified parameters are outputted to the various hearing devices to change the acoustic and/or electric stimulation parameters of the various hearing devices.

Figure 8:
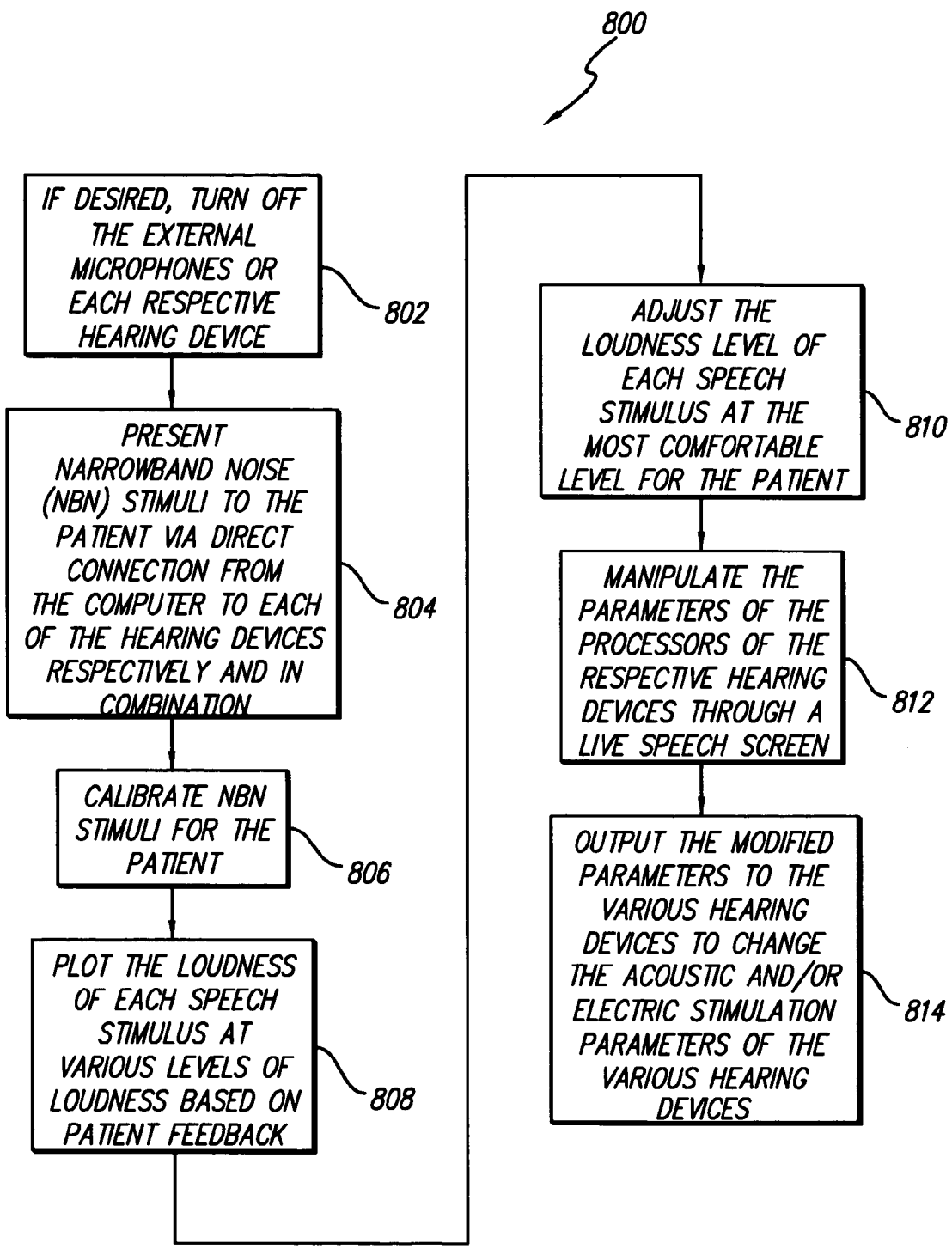
FIG. 8 is a flowchart of another example paradigm for the method of FIG. 6.

Referring to FIG. 8, in another example embodiment, a paradigm 800 includes the following steps which can be performed in any enabling order. At step 802, if desired, the external microphones of each respective hearing device are turned off so as to avoid unwanted environmental noise and sounds. At step 804, narrowband noise (NBN) stimuli are presented (e.g., at octave and inter-octave intervals from audio files on a computer, or a loudspeaker) to the patient via direct connection from the computer to each of the hearing devices respectively and in combination. At step 806, NBN stimuli are calibrated in decibel sound pressure level (dBSPL) for the patient. At step 808, the loudness of each speech stimulus at various levels of loudness based on patient feedback is plotted. At step 810, the loudness level of each speech stimulus is adjusted at the most comfortable level for the patient. At step 812, the parameters of the processors of the respective hearing devices are manipulated through a live speech screen, e.g., shown in the output adjustment window of a software program presented on the computer. At step 814, the modified parameters are outputted to the various hearing devices to change the acoustic and/or electric stimulation parameters of the various hearing devices.

While the invention herein disclosed has been described by means of specific embodiments and applications thereof, numerous modifications and variations could be made thereto by those skilled in the art without departing from the scope of the invention set forth in the claims.

What is claimed is:

1. A method for modifying the parameters of at least one hearing device, comprising:
   receiving electric and acoustic stimulation data from at least one hearing device to a computer with software;
   assessing electric and acoustic stimulation parameters and patterns based on the stimulation data including assessing the proper sequencing of acoustic and electric events;
   delivering the electric and acoustic stimulation parameters and patterns to the at least one hearing device; and
   mapping the stimulation data with the software to one or more stimulation channels to selectively create a stimulation site located at one of the stimulation channels or between two of the stimulation channels.

2. The method of claim 1, wherein:
assessing electric and acoustic stimulation parameters and patterns based on the stimulation data includes assessing the proper sequencing of acoustic and electric events for at least one of a hearing aid and the acoustic elements of an electric-acoustic processor and at least one of a cochlear implant speech processor and the electric elements of an electric-acoustic processor.

3. The method of claim 1, wherein:
assessing electric and acoustic stimulation parameters and patterns based on the stimulation data includes assessing the proper sequencing of acoustic and electric events for a hearing aid and a cochlear implant speech processor.

4. The method of claim 1, wherein:
assessing electric and acoustic stimulation parameters and patterns based on the stimulation data includes assessing the proper sequencing of acoustic and electric events for a hearing aid and the electric elements of an electric-acoustic processor.

5. The method of claim 1, wherein:
assessing electric and acoustic stimulation parameters and patterns based on the stimulation data includes assessing the proper sequencing of acoustic and electric events for the acoustic elements of an electric-acoustic processor and a cochlear implant speech processor.

6. The method of claim 1, wherein:
assessing electric and acoustic stimulation parameters and patterns based on the stimulation data includes assessing the proper sequencing of acoustic and electric events for the acoustic and electric elements of an electric-acoustic processor.

7. The method of claim 1, wherein:
delivering the electric and acoustic stimulation parameters and patterns to the at least one hearing device includes at least one of simultaneously and sequentially outputting instructions capable of modifying acoustic and electric parameters to determine interaction between multiple channels in at least one of a hearing aid, the acoustic elements of an electric-acoustic processor, a cochlear implant speech processor, and the electric elements of an electric-acoustic processor.

8. The method of claim 1, wherein:
delivering the electric and acoustic stimulation parameters and patterns to the at least one hearing device includes simultaneously outputting instructions capable of modifying acoustic and electric parameters to determine interaction between multiple channels in at least one of a hearing aid, the acoustic elements of an electric-acoustic processor, a cochlear implant speech processor, and the electric elements of an electric-acoustic processor.

9. The method of claim 1, wherein:
delivering the electric and acoustic stimulation parameters and patterns to the at least one hearing device includes sequentially outputting instructions capable of modifying acoustic and electric parameters to determine interaction between multiple channels in at least one of a hearing aid, the acoustic elements of an electric-acoustic processor, a cochlear implant speech processor, and the electric elements of an electric-acoustic processor.

10. The method of claim 1, wherein:
the at least one hearing device comprises two hearing devices configured to be worn contralateral to each other by a patient.

* * * * *